(12) United States Patent
Ishikawa et al.

(10) Patent No.: US 6,645,179 B1
(45) Date of Patent: *Nov. 11, 2003

(54) INJECTION SYRINGE

(75) Inventors: Hiromichi Ishikawa, Kobe (JP); Shinichi Koni, Takarazuka (JP)

(73) Assignee: Nihon Chemical Research Co., Ltd., Ashiya (JP)

( * ) Notice: Subject to any disclaimer, the term of this patent is extended or adjusted under 35 U.S.C. 154(b) by 266 days.

This patent is subject to a terminal disclaimer.

(21) Appl. No.: 09/611,660

(22) Filed: Jul. 6, 2000

(30) Foreign Application Priority Data

Jul. 6, 1999 (JP) .......................................... 11-192124

(51) Int. Cl.⁷ ................................................ A61M 5/00
(52) U.S. Cl. .......................... 604/181; 604/82; 604/89; 604/191; 604/90
(58) Field of Search ............................... 604/82, 89, 90, 604/181, 187, 191, 83, 84, 85, 88, 92, 200, 205, 207, 188, 212–214

(56) References Cited

U.S. PATENT DOCUMENTS

| | | | | |
|---|---|---|---|---|
| 5,171,220 A | * | 12/1992 | Morimoto | 604/88 |
| 5,281,198 A | * | 1/1994 | Haber et al. | 604/86 |
| 5,549,561 A | * | 8/1996 | Hjertman | 604/131 |
| 5,569,191 A | * | 10/1996 | Meyer | 604/82 |
| 5,630,800 A | * | 5/1997 | Blank et al. | 604/82 |
| 5,807,323 A | * | 9/1998 | Kriesel et al. | 604/89 |
| 6,319,225 B1 | * | 11/2001 | Sugita et al. | 604/89 |

\* cited by examiner

Primary Examiner—Thomas Denion
Assistant Examiner—Bimh Tran
(74) Attorney, Agent, or Firm—Oblon, Spivak, McClelland, Maier & Neustadt, P.C.

(57) ABSTRACT

An injection syringe generally comprised of a multichambered cylindrical ampule, a tripartite case of a front case; a middle case; a rear case, and a needle-holder, and a plunger: the multichambered cylindrical ampule including two chambers of a front space and a rear space, the front space being sealed forwardly with a packing penetrable by a needle and sealed rearwardly with a movable front gasket, and the rear space being sealed forwardly with the front gasket and sealed rearwardly with a movable rear gasket, and the ampule also including a bypass route longitudinally arranged on inner surface of the ampule such that the front gasket is located to take a position rearwardly apart from the bypass route before dissolution of a solid medicine, wherein the front space for admission of the solid medicine is separated from the rear space for admission of a medicinal solvent or dispersing agent; the middle case also including a short thread or fixer means provided externally at midportion thereof, and the rear case including another short thread or fixer means provided internally at the front end thereof. The present invention brings out the merits of facilitating injections in the use of unstable chemicals, and avoiding possible inclusion of foreign matters or microorganisms, and overcoming misoperations possible during complex preparation procedure, inability to comply with an urgent case, such are attendant defects with traditional injection syringes.

3 Claims, 7 Drawing Sheets

INJECTION SYRINGE

FIELD OF THE INVENTION

The present invention relates to an injection syringe including a device for preparation of an injection (plural: injections). More particularly, the present invention relates to an injection syringe provided with a structure in which an unstable freeze dried medicine and a medicinal solvent are stored in separate spaces and an injection is readily prepared by dissolution of the unstable freeze dried medicine into the medicinal solvent as necessary in situ, in place of the conventional preparation that the unstable freeze dried medicine and the medicinal solvent have been stored in traditional vials.

The present invention is applicable to a wide range of chemicals traditionally stored in vials, and is also applicable to such unstable chemicals as will suffer chemical changes if stored in the status of solution or dispersion for a long period. Thereby, a patient who is required to carry the injection kit with him and perform the injection for himself is conveniently enabled to do so, wherein the control of a dosage is also enabled.

DESCRIPTION OF THE RELATED ART

Conventionally, chemicals for injection use have been stored in the sterile environment or sealed in vials. In preparing the injection, the solvent is taken up from the solvent vial and charged into the solid medicine vial for dissolution. However, such operation possibly includes chances to attract microorganisms, fine foreign matters such as fine glass or rubber fragments. Further, the transfer act of the dissolution stored in the vial to the injection syringe has sometimes suffered from misoperations. In addition, it has taken a considerable time to finish the preparation for the injection, difficult to comply with an urgent case, and a wide space is required to support such operations because a number of vessels or tools are involved.

Traditionally, where a patient has to sit for injections regularly for a long period, for instance, injections of human growth hormones or insulin, such system has been employed as the patient always carries the kit of injection syringe and performs injections for himself. In this application, an injection syringe should be ready to be assembled by himself and there has been known the injection syringe for multiple usage by exchange of the ampule and the needle.

SUMMARY OF THE INVENTION

Heretofore, when a unstable freeze dried medicine after dissolution is difficult to store for long time, the medicine and the solvent therefor have been stored in vials separately. The injection is prepared with use of the vials and thereafter transferred to the injection syringe to perform the injection. The task has remained in the point of facilitating traditional operations and avoiding possible inclusion of foreign matters or microorganisms, and overcoming misoperations possible during complex procedure, inability to comply with an urgent case, the present invention is intended to develop the apparatus and process for storing the medicine and the solvent separately inside the injection syringe to prepare for the injection also inside the same injection syringe. The consequent injection should be applicable in situ as necessary.

In view of such task as noted above, the present invention is accomplished with start from the multichambered injection syringe used to unstable substances, such as human growth hormones, interferon, other polypeptides and by adding some simple structures to such injection syringe, including a device for accommodating the cylindrical ampule inside the injection apparatus, and a device for storing the injection without a reverse flow occurring in the ampule interior during the time from the preparation of the injection to the performance of the injection, and a device for ready performance in situ as necessary, further devices such as for adjusting a dosage amount as well as for connecting the injection syringe with the tridirectional valve.

BRIEF DESCRIPTION OF THE DRAWING

FIG. 1 shows an embodiment of the present invention wherein FIG. 1(a) is a schematic front view and FIG. 1(b) is a sectional view sectioned along A–A' line (shown in FIG. 1(a)) at the status before the dissolution step.

FIG. 2 relates to the same embodiment covered by FIG. 1, wherein FIG. 2(a) is the same sectional view as FIG. 1(b) at the status after the dissolution step, and FIG. 2(b) is a sectional view sectioned along B–B' line (shown in FIG. 1(a)).

FIG. 3 shows a modified embodiment of the inventive injection syringe, wherein FIG. 3(a) shows the status before the dissolution of the unstable freeze dried medicine in longitudinally sectioned view, and FIG. 3(b) shows the status after the dissolution is complete also in longitudinally sectioned view.

FIG. 4 shows a further modified embodiment of the inventive injection syringe, wherein FIG. 4(a) shows the status before the dissolution of the unstable freeze dried medicine in longitudinally sectioned view, and FIG. 4(b) shows the status after the dissolution is complete also in longitudinally sectioned view.

FIG. 5 shows a still further modified embodiment of the inventive injection syringe, wherein FIG. 5(a) shows the status before the dissolution of the unstable freeze dried medicine in longitudinally sectioned view, and FIG. 5(b) shows the status after the dissolution is complete also in longitudinally sectioned view.

FIG. 6 shows another still further modified embodiment of the inventive injection syringe, wherein FIG. 6(a) shows the status before the dissolution of the unstable freeze dried medicine in longitudinally sectioned view, and FIG. 6(b) shows the status after the dissolution is complete also in longitudinally sectioned view.

FIG. 7 shows the structure of the locking nut 39 included in the embodiment shown by FIG. 6, wherein: FIG. 7(a) shows a schematic front view thereof; FIG. 7(b) shows a schematic sectional view sectioned along the line A–A' in FIG. 7(a); FIG. 7(c) shows a schematic sectional view sectioned along the line B–B' in FIG. 7(b).

DETAILED DESCRIPTION OF THE INVENTION

An injection syringe 1 of the invention for an unstable freeze dried medicine is generally comprised of a multi-chambered cylindrical ampule 2, a tripartite case of a front case 3; a middle case 4; a rear case 5, and a needle holder 6, and a plunger 7:

(1) the multichambered cylindrical ampule 2 including two chambers of a front space 8 and a rear space 9, the front space 8 being sealed forwardly with a packing 10 penetrable by a needle 25 and sealed rearwardly with a movable front gasket 11, and the rear space 9 being sealed forwardly with the front gasket 11 and sealed rearwardly with a movable rear gasket 12, and the ampule 2 also including a bypass route 13 longitudinally arranged on inner surface of the ampule 2 such that the front gasket 11 is located to take a position rearwardly apart from the bypass route 13 before dissolution of an unstable freeze dried medicine 14 wherein the front space 8 for admission of the unstable freeze dried medicine 14 is separated from the rear space 9 for admission of a medicinal solvent 15 or dispersing agent 15, thereby the unstable freeze dried medicine 14 and the solvent 15 or dispersing agent 15 being separately stored;

(2) the front case 3 including a tapered tip portion to fix the front edge of the ampule 2 inside thereof, and a thread or fixer means 16 provided externally at the rear end thereof; the middle case 4 including another thread or fixer means 16' provided internally at the front end thereof, and a flange 18 provided internally at the rear end thereof to fixedly accommodate the ampule 2 inside a housing formed of the front case 3 and the middle case 4 by tightening the thread or fixer means 16, 16';

(3) the middle case 4 also including a short thread or fixer means 19 provided externally at midportion thereof, and the rear case 5 including another short thread or fixer means 19' provided internally at the front end thereof, and also a plunger retainer 20 provided internally at the rear end thereof, the plunger 7 being mounted in place by the retainer 20 and engaged at its front end with a rear gasket 12;

(4) wherein, in a process of dissolving the solid medicine 14, pushing on the rear case 5 toward the front of the ampule 2 causes the front gasket 11 and the rear gasket 12 in unison to advance with aid of abutment at a shoulder 24 provided at midportion of the plunger 7; upon the front gasket 11's entry into the bypass route 13's zone, the solvent or dispersing agent 15 stored in the rear space 9 starts flowing into the front space 8 through the bypass route 13 and an injection is prepared after the medicine 14 has been dissolved or dispersed; then, tightening the short thread or fixer means 19, 19' to connect the middle case 4 with the rear case 5 avoids a reverse move of the shoulder 24 with aid of the retainer 20 to keep the injection at its complete status; further, mounting a needle holder 6 on the packing 10 before or after the injection preparation, and pushing on the rear end 21 of the plunger 7 performs the injection through the needle holder 6, thereby completing the injection with use of an unstable injection.

Figure 3:
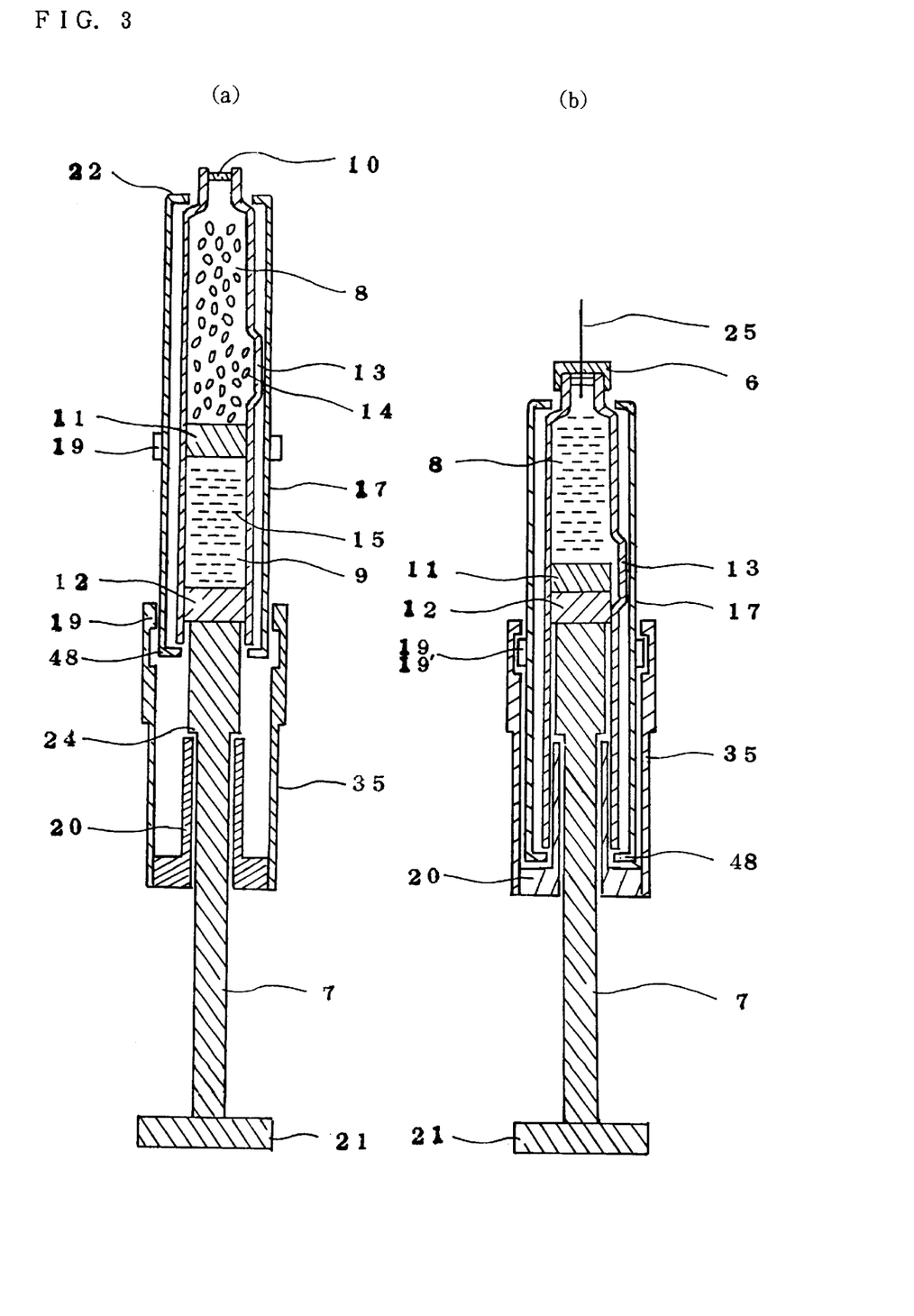

In connection with the basic embodiment as noted above, the present invention includes a modification such that the front case 3 and the middle case 4 are integrated to internally accommodate and fix the ampule 2, that is to see FIG. 3, such a case may be referred to as a front case 17 which is engaged with a rear case 35 to compose the bipartite case, more compact embodiment. In this modification, in a process of dissolving the solid medicine 14, pushing on the rear case 17 toward the front of the ampule 2 causes the front gasket 11 and the rear gasket 12 in unison to advance with aid of abutment at a shoulder 24 provided at midportion of the plunger 7; upon the front gasket 11's entry into the bypass route 13's zone, the solvent or dispersing agent 15 stored in the rear space 9 starts flowing into the front space 8 through the bypass route 13 and an injection is prepared after the medicine 14 has been dissolved or dispersed; then, tightening the short thread or fixer means 19, 19' at the place 19 to connect the front case 17 with the rear case 35 avoids a reverse move of the plunger 7 with aid of the retainer 20 to keep the injection at its complete status, further, mounting a needle holder 6 on the packing 10 before or after the injection preparation, and pushing on the rear end 21 of the plunger 7 performs the injection through the needle holder 6.

In connection with the basic embodiment, the present invention includes a further modification such that a plunger 27 is provided with circumferential grooves 29 in stepwise arrangement at its midportion and also a plunger retainer 28 is provided with nail or ratchet 30 at its inner most portion so as to mesh with the grooves 29. That is to see FIG. 4. In this modification, the injection status after preparation is kept by the fit between the fixer means 19, 19' on the engaged cases, and this nail's and groove's meshing mechanism acts as reverse detente against a backward move of the plunger 27 which is possible in the course of performing the injection due to back pressure occurred in the injection.

Figure 4:
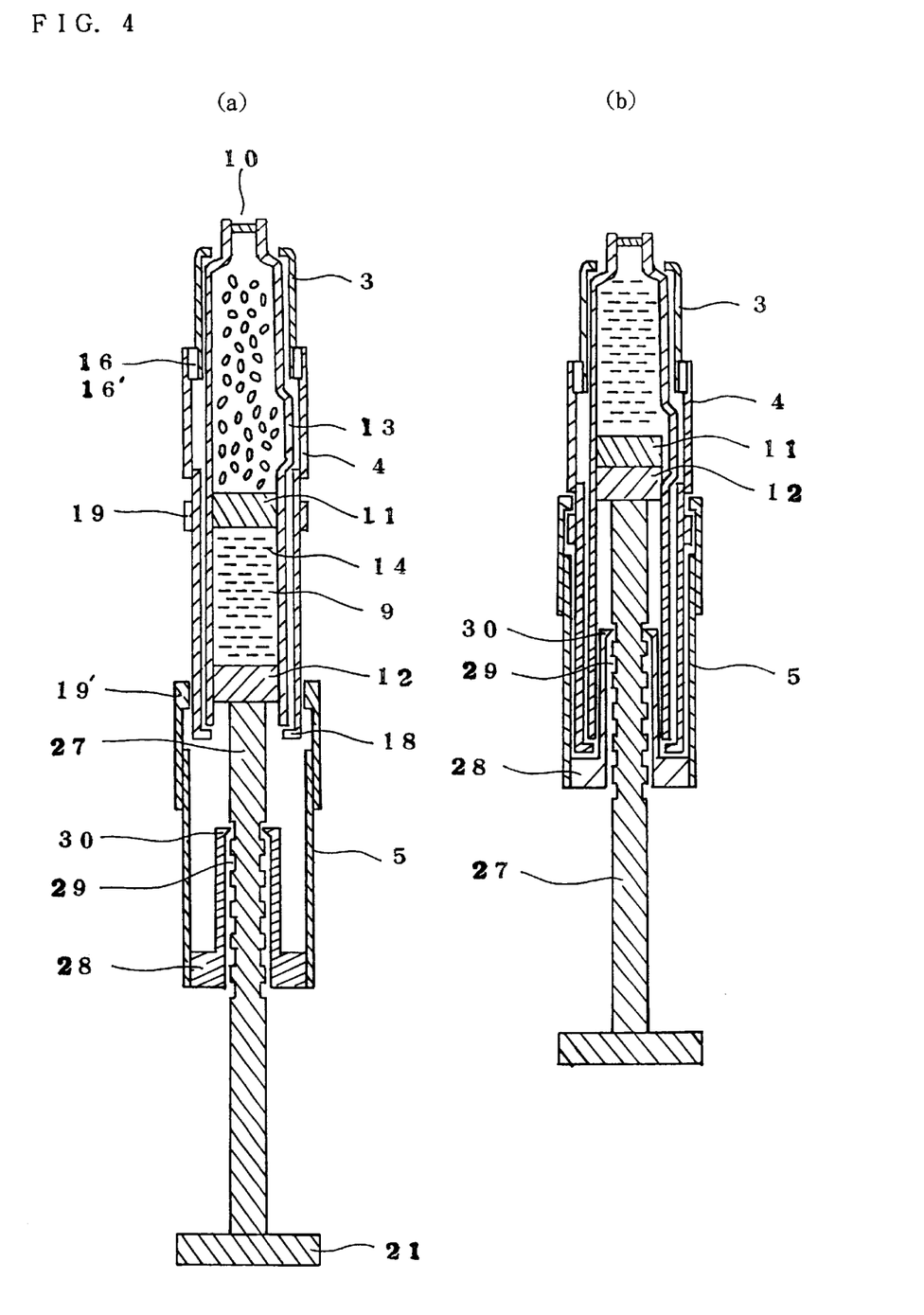

In performing the injection, pushing on the rear end 21 of the plunger 27 advances the plunger 27 forwardly (upward move from the status shown in FIG. 4(*b*)) with snapping or sliding through the hole formed in the ratchet 30.

In connection with the embodiment, the present invention includes a further modification such that a plunger 32 is provided with thread portion 33 covering the length from its rear end to midpoint, and a ring nut 34 having another thread 33' for determining an injection amount is provided to mesh with the thread portion 33. That is to see FIG. 5. The injection status after the preparation is kept by the fit between fixer means 19, 19' of the front and middle cases 3, 4 with aid of abutment at the shoulder 31.

Figure 5:
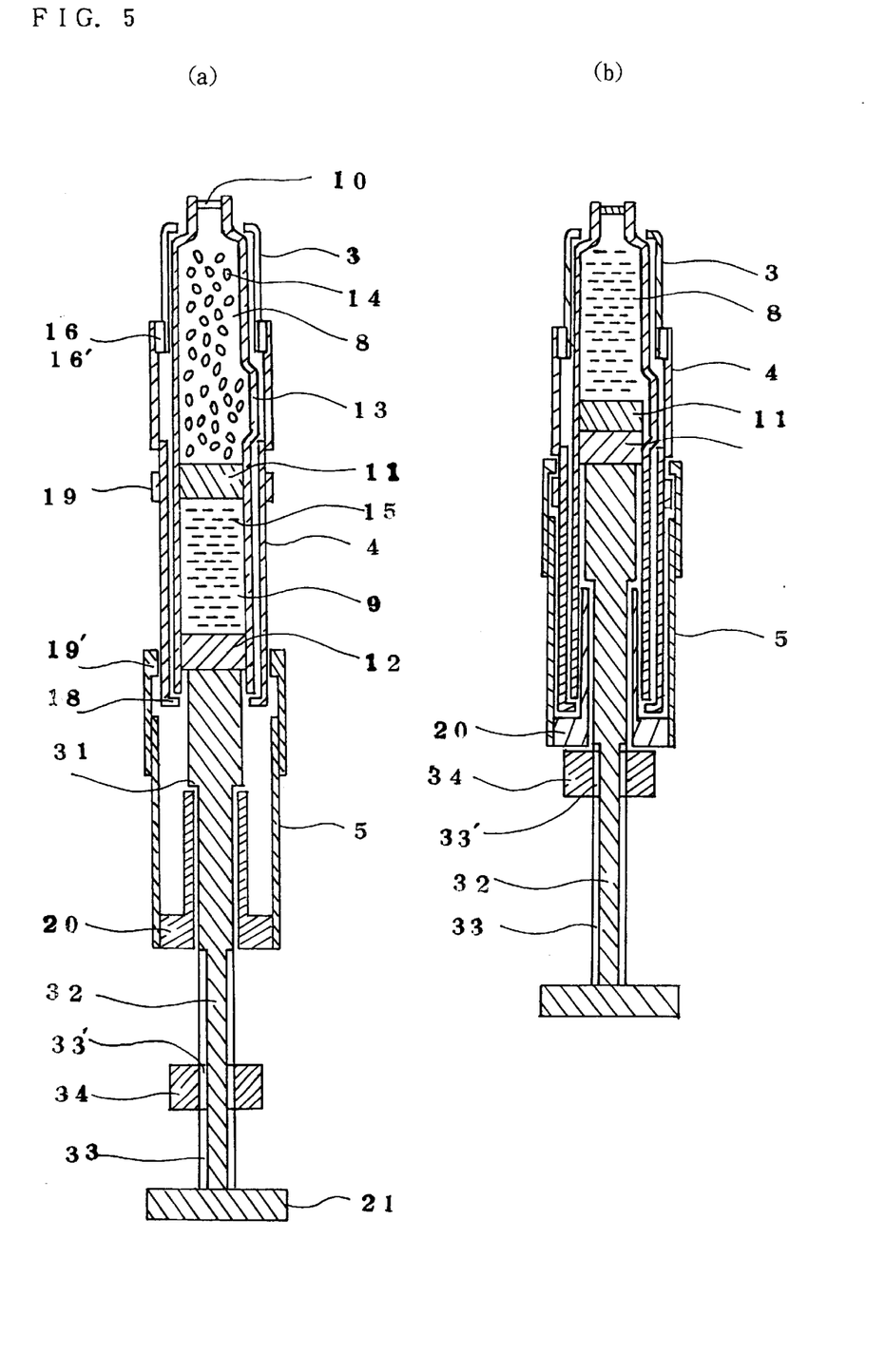

In performing the injection, determination of an injection amount or dosage is permitted by adjusting or setting the position of the ring nut 34, and then, pushing on the rear end 21 of the plunger 32 to the stop point set by the ring nut 34 performs the injection with a predetermined dosage.

The present invention includes a still further modification such that an injection syringe including a multichambered cylindrical ampule 2, an outer case 37, a needle holder 6, a plunger 36, wherein the ampule 2 and the needle holder 6 are the same as those noted above, but the outer case 37 for accommodating the ampule 2 is unipartite or one-piece. That is to see FIG. 6. As shown, the plunger 36 has the front end engaged with the rear gasket 12, and is mounted with a locking nut 39 to seal the rear end of the outer case 37 as well as to place the plunger 36 for determination of an injection dosage. In this modification, the status before or after the dissolution taking place in the ampule 2 is kept by locking function of the nut 39.

Figure 6:
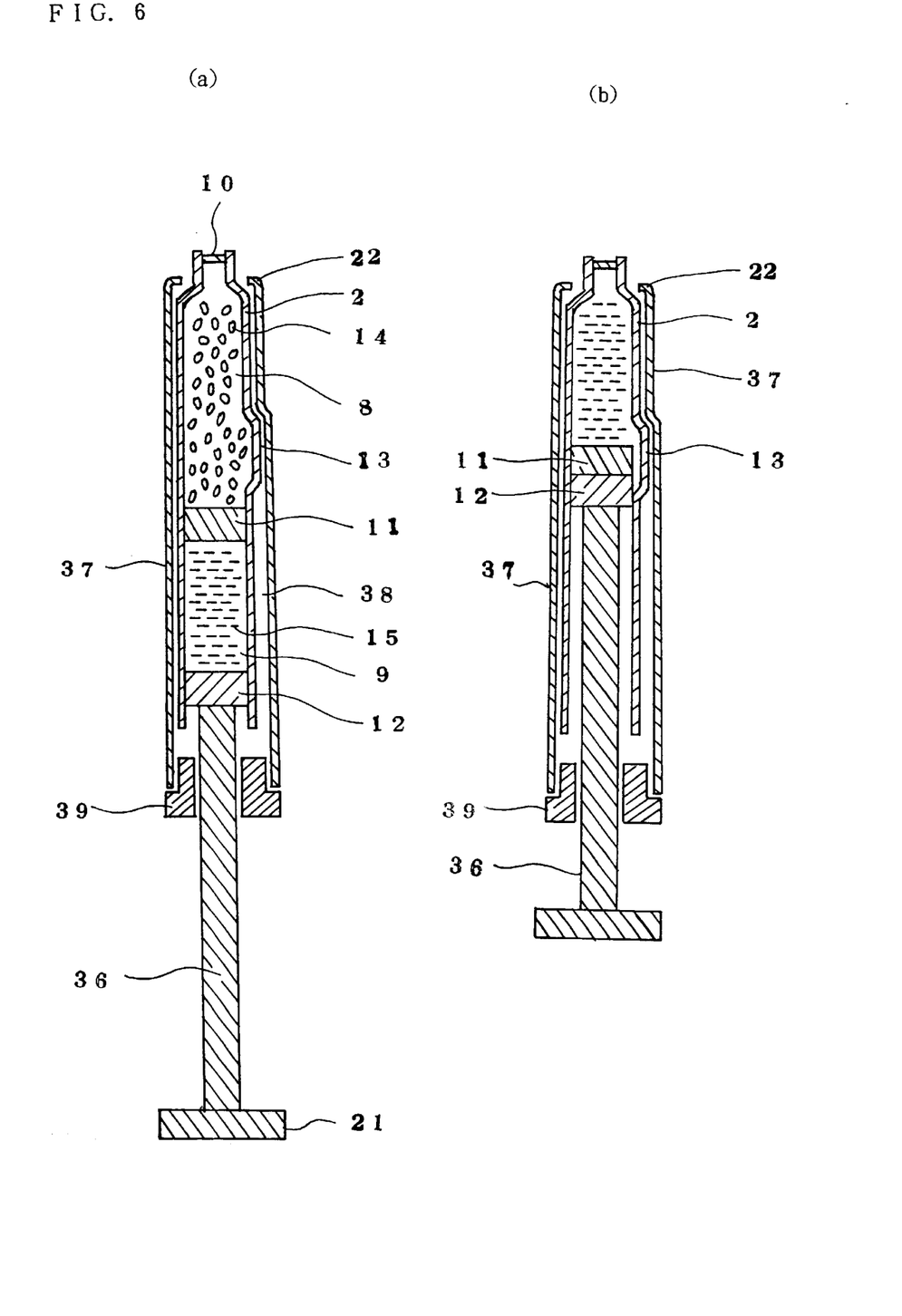

In dissolving the unstable freeze dried medicine, the nut 39 is unlocked, and pushing on the rear gaskets 11, 12 to advance in unison. Upon the front gasket 11's entry into the bypass route 13's zone, the solvent or dispersing agent 15 stored in the rear space 9 starts flowing into the front space 8 through the bypass route 13 and the injection is prepared after the medicine 14 has been dissolved or dispersed. Locking the nut 39 fixes the plunger 36 and the outer case 37 to avoid the gasket 12 from a backward move. The complete status of the injection is kept thereby.

In performing the injection, the nut 39 is set at a position to determine the dosage, and pushing on the rear end 21 of the nut 39 to the stop point set at the rear end of the outer case 37 performs the injection through the needle holder 6.

In this modification, it is preferable to provide a bypass receiving recess 38 longitudinally on the internal surface of the outer case 37 to avoid a rotational move of the ampule 2 inside the outer case 37. Additionally, in any embodiments so far, the present invention includes an injection syringe provided with a needle holder 6 whose needle is converted to a circular cone shaped nozzle for the purpose of obtaining fitness to a tridirectional valve leading to a catheter. In the following, the present invention will be described in more details.

Herein, the term "solvent or dispersing agent" is used for the reason that normally an unstable freeze dried medicine is dissolved in water, but sometimes an injection is prepared to be an emulsion or dispersion according to the property of the unstable freeze dried medicine. In the following, the term "solvent" will sometimes represent a solvent as well as a dispersing agent. And the term "bypass zone" means a zone that the front gasket as a whole has entered into the bypass length and a solvent stored in the rear space is allowed to flow into the bypass route.

The term "short thread or fixer means" in the above includes a means for connecting the two cases, but it means scarce capability of advancing the middle case or rear case. "Fixer means" indicates any means for fixing the two cases without limit in its structures, including hook, worm device. Further, in the above, the ring nut 34 or the locking nut 39 is used to set or adjust a dosage amount. This implies that the injection will sometimes be performed more than one time using the same injection. However, mostly the injection finishes one time. For instance, if 70% of the injection will be injected and 30% thereof is excess, the excess 30% is normally cast away prior to the injection. In such a case, the nut 34 or 39 is useful to set an amount for casting away. The present invention includes such a preliminary operation.

Figure 7:
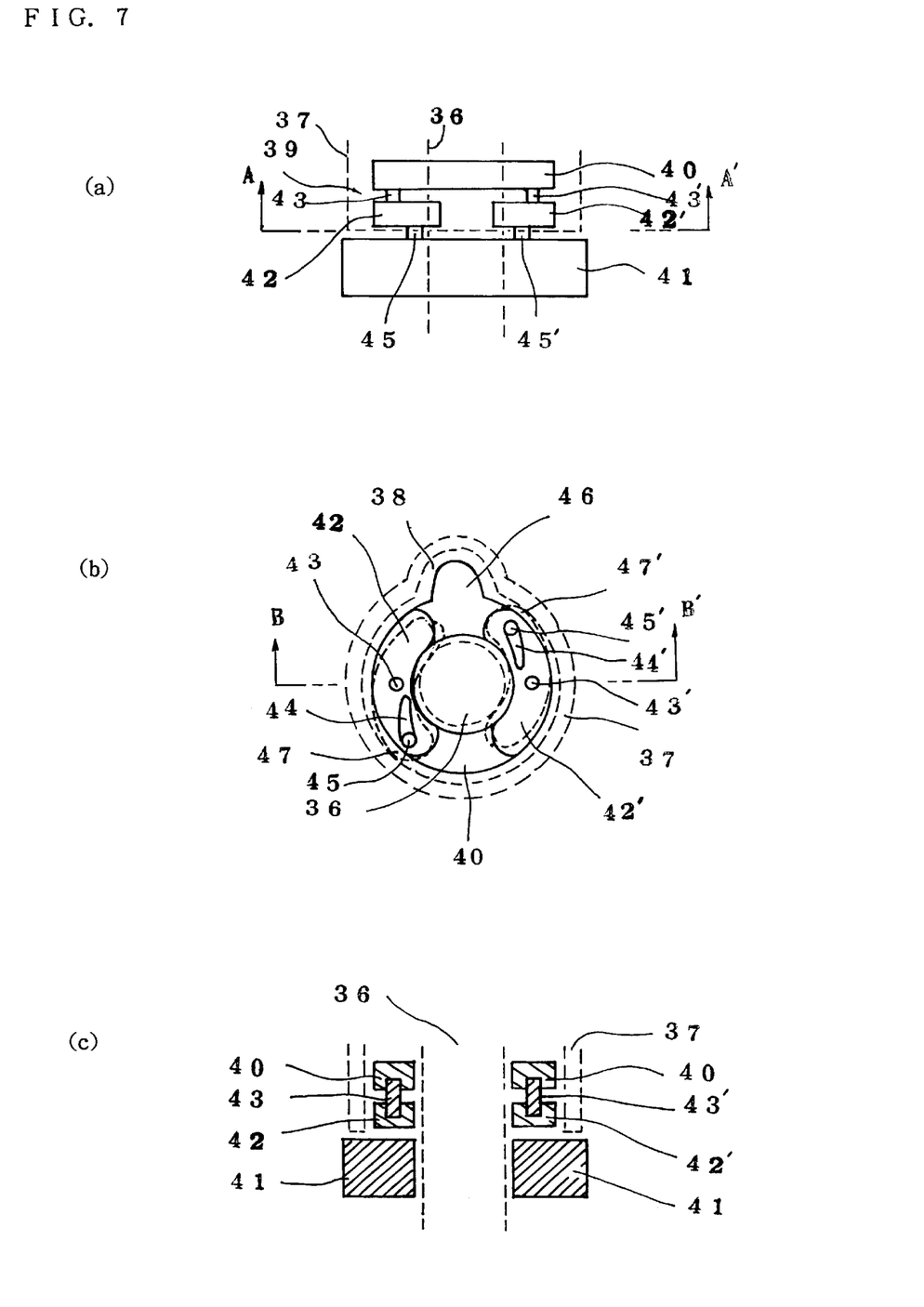

The term "locking nut" in the above will be exemplarily shown in FIG. 7, which does not limit the term "locking nut," however. Any means is acceptable if it performs the locking between the plunger 36 and the outer case 37 or the locking between the locking nut 39 and the plunger 36 to set a dosage amount.

As for materials to produce the inventive injection syringes, plastic or rubber materials are preferable wherein glass is partly preferable. Of them, preferable are: the multichambered ampule cylinder is made from glass, the gasket is from synthetic rubber (nitrile rubber, silicone rubber, isoprene rubber, butadiene rubber, styrene/butadiene rubber, butyl rubber, chloroprene rubber). The case including the front, middle, rear ones is from AS resin (styrene/acrylonitrile copolymer, it will be noted "AS") or acrylic resin. The plunger is from polypropylene. Other applicable materials are ABS resin (styrene/butadiene/acrylonitrile copolymer, it will be noted "ABS"), polyethylene, polystyrene, polycarbonate, cycloolefine copolymer, polyethylene terephthalate, polyvinyl chloride resin, and metals.

The present invention includes the multichambered cylindrical ampule and is not limited to an ampule having a plurality of inner spaces. However, in most cases, two inner spaces are convenient.

Heretofore, the use of vials, well known vessel for handling chemicals for injections, has been customary when the preparation of an injection is attempted. Specifically, an unstable freeze dried medicine is stored in a vial, and in preparing an injection as necessary, an amount of the solvent is transferred from the solvent vial to the vial of the unstable freeze dried medicine by an appropriate tool to form the dissolution or the injection. Then, a necessary amount is taken up into an injection syringe for injection. On the other hand, heretofore, a multichambered ampule has been developed and used for such a patient as is required to carry an injection kit for the purpose of facilitating the use of an unstable or environmentally sensitive medicine, such as human growth hormones, as well as performing the injection for himself in situ. The present invention deserves achievement improved from the vial-handled preparation to the preparation in an injection syringe. Accordingly, the present invention is applicable widely to the field of the vial-handled injection preparation.

Further, the present invention is applicable to long time storing of such medical substances at its solution status as are difficult to do so due to chemically unstable nature, such as human growth hormones, interferon, other polypeptides. However, these substances are subject to suffer unnegligible chemical changes if stirring or shake, or flow disturbance or other physical force is affected. For this reason, the process of dissolving the solid medicine with the solvent requires avoiding the stirring or flow disturbance involving the substances being handled.

In performing the dissolution using the inventive injection syringe, normally the needle holder is not mounted at the front of the injection syringe, and the rear end of the ampule is engaged with the plunger and then, the plunger's rear end is slowly pushed manually. Upon the front gasket's entry into the bypass zone, the solvent stored in the rear space starts flowing into the front space to the dissolution, wherein a flow rate is monitored and controlled manually by observation of a dissolving condition of aid medicine, maintained in a laminar flow state so as not to cause stirring and shaking during the dissolution. In this process, care should be taken to the binding condition that the involved substances are subject to suffer unnegligible chemical changes from physical force. Good care should be taken particularly to stirring or flow disturbance.

To practice the manual pushing as noted above, methodologically preferable is to erect the syringe vertically to be the front up on a desk or plane and press the syringe downwardly from above to move the gaskets 11, 12 relatively upward. In this process of dissolution, possibly remnant gas would collect at the top end of the ampule and develop to a back pressure. But tightening the fixer means 19, 19' provided at engaging portion between the middle and rear cases 4, 5, after the dissolution, avoids a reverse move of the plunger 7 with aid of the abutment between the shoulder 24, 31 and the plunger retainer 20, 28 so that the injection is kept in the status complete of dissolution. Then, the present invention includes a process of dissolution after the needle holder is mounted. It is choice as necessary.

EXAMPLE 1

Figure 1:
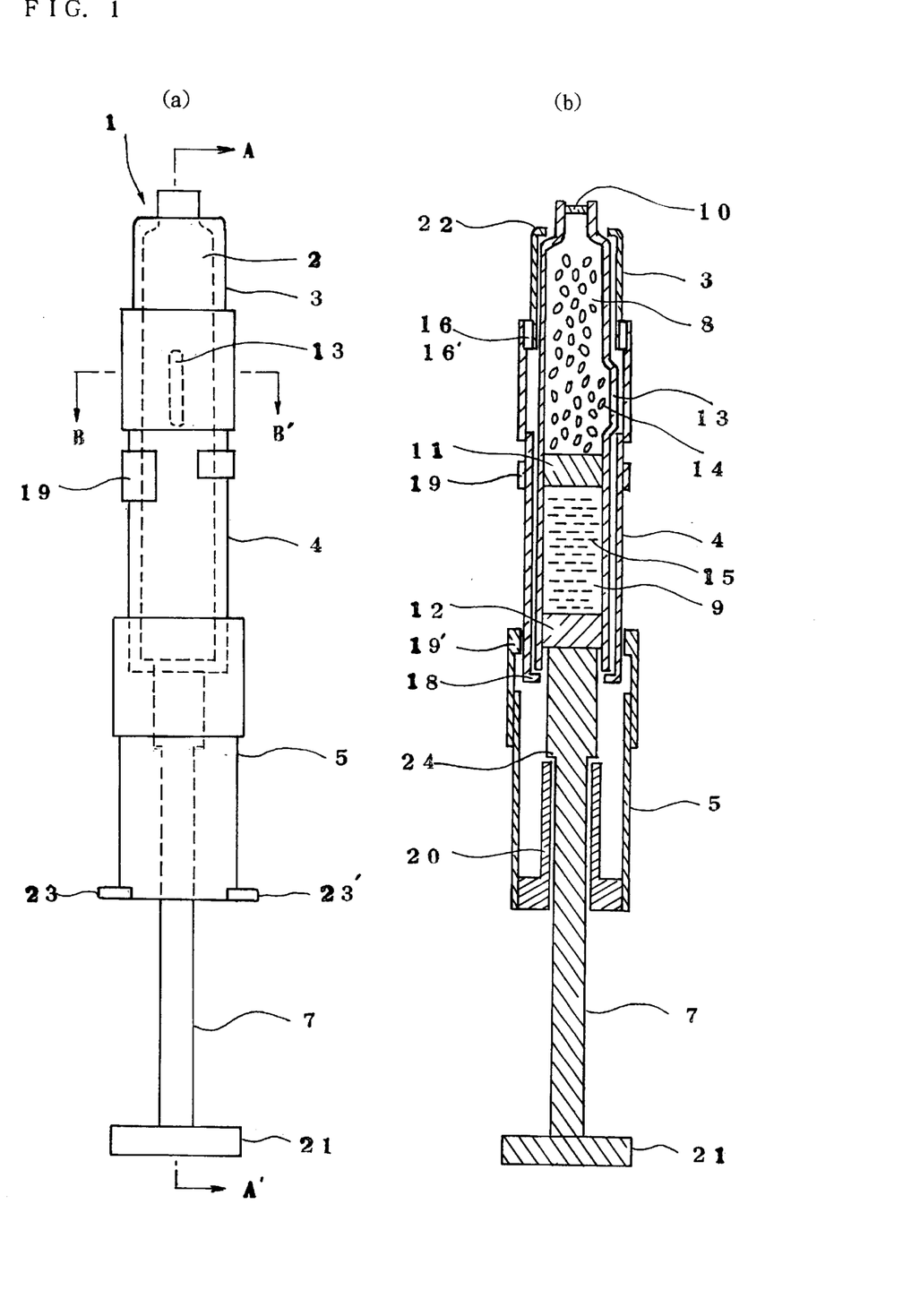
Figure 2:
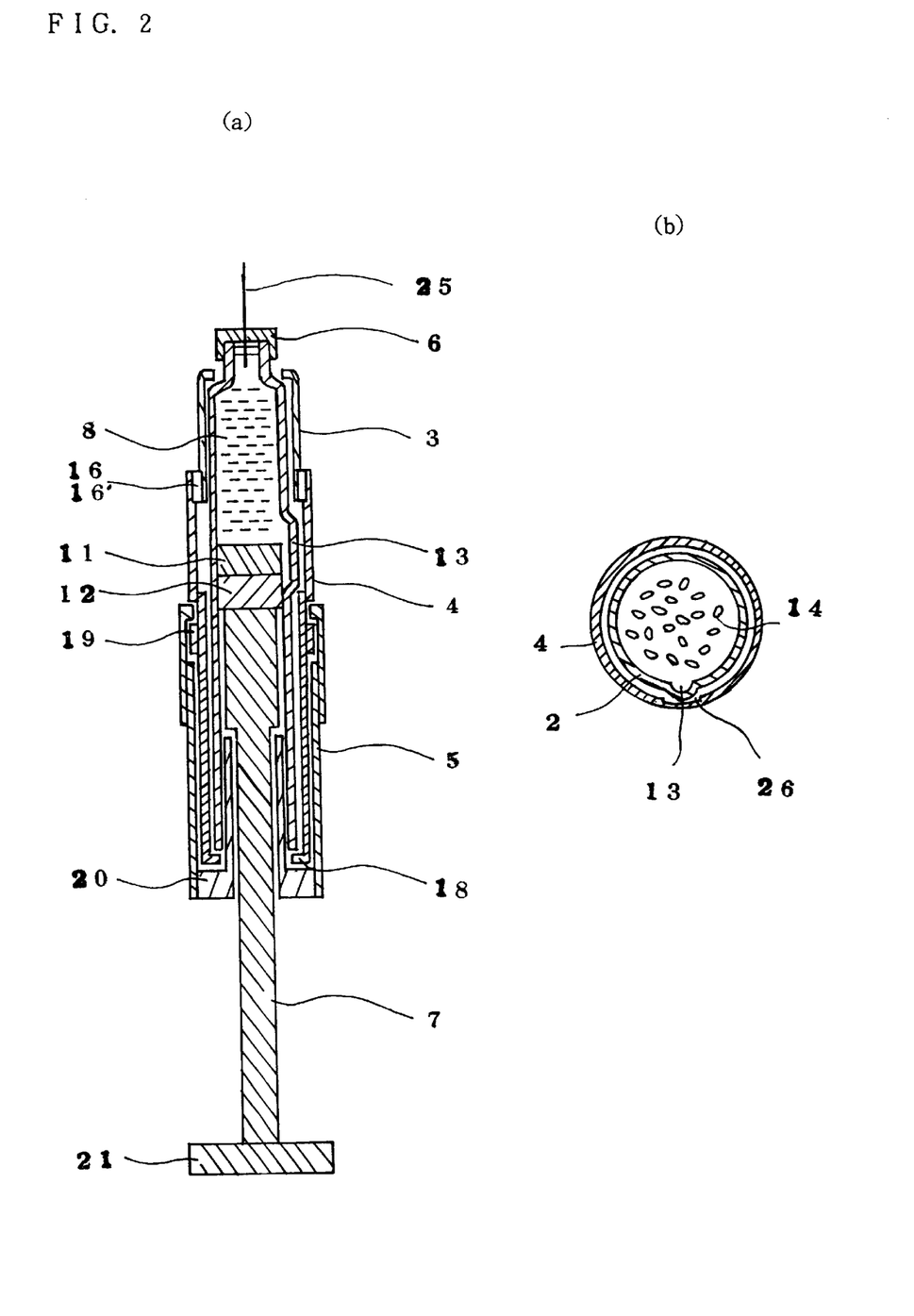

Next, detailed structures and functions of the inventive injection syringe including a device for preparation of an injection will be described with reference to the drawings. FIG. 1 shows an embodiment of the present invention wherein FIG. 1 shows an embodiment of the present invention wherein FIG. 1(*a*) is a schematic front view and FIG. 1(*b*) is a sectional view sectioned along A–A' line (shown in FIG. 1(*a*)) at the status before the dissolution step. FIG. 2(*a*) is the same sectional view as FIG. 1(*b*) at the status after the dissolution step with a needle holder is mounted, and FIG. 2(*b*) is a sectional view sectioned along B–B' line (shown in FIG. 1(*a*)).

Materials applied to the main portions of the syringe are: a multichambered cylindrical ampule 2 is made from glass, gaskets 11, 12 are from synthetic rubber, front and middle cases 3, 4 are from AS resin, a rear case is from acrylic resin, a plunger 7 is from polypropylene.

The two chambered ampule 2 includes a front space 8 and a rear space 9. The front space 8 is sealed forwardly with a packing 10 mounted at an exit mouth, extreme top portion in view, and sealed rearwardly with a movable front gasket 11. The rear space 9 is sealed forwardly with a front gasket 11 and sealed rearwardly with a movable rear gasket 12. The ampule 2 also includes a bypass route 13 longitudinally arranged on inner surface of the ampule 2 such that the front gasket 11 is located to take a position rearwardly apart from the bypass route 13, in other words, located clear of the bypass route 13 before dissolution of an unstable freeze dried medicine 14, that is, the unstable freeze dried medicine 14 charged in the front space 8 is separated from a medicinal solvent 15 or dispersing agent 15 charged in the rear space 9.

The ampule 2 is sheathed or inset inside the front and middle cases 3, 4 which are engaged with meshing between a thread 16 provided externally at the rear end of the front case 4 and a thread 16' provided internally at the front end of the rear case 5. Interior of the connected space, the ampule 2 is accommodated. In place of the threads 16, 16', another functionally similar means represented by 19, 19' is applicable, as shown in FIGS. 1(a) and (b). The front case 3 has a tapered tip end 22 by which the ampule 2 is fixed at its front edge, and the middle case 4 has an inward flange 18 at its rear end by which the ampule 2 is fixed at its rear edge. Further, as illustrated in FIG. 2(b), provision of a recess 26 internally on inner surface of the middle case 4 covering the length of the bypass route 13 avoids the ampule 2 from a free rotation.

The middle case 4 has the fixer means 19 externally on its cylindrical surface, and the rear case 5 has the fixer means 19' internally on its cylindrical surface and also has externally at the rear end projections 23, 23' to be used as hook for fingers in performing an injection. Further, internally at the rear end a plunger retainer 20 is mounted to hold the plunger 7 with telescopic movability. The plunger 7 has the front end engaged with the rear gasket 12 and has a shoulder 24 at its midportion. Further, the plunger 7 has a rear end 21 shaped for convenience in gripping by hand which is expected in performing the injection.

At the start of actuating the injection syringe, pushing forwardly on the rear end 21 of the plunger 7 causes the rear gasket 12 to advance. In turn, the solvent 15 stored in the rear space 9 flows into the front space 8 and thereby the medicine 14 is dissolved to be the injection. This actuation or the pushing is preferably performed at such status that the syringe 1 is erected vertically on a desk or a plane with press on the syringe 1 downwardly from above so that the gaskets 11, 12 move slowly upward in relation to the ampule 2, upon the front gasket 11's entry into the bypass route 13's zone, the solvent 15 stored in the rear space 9 starts flowing into the front space 8 through the bypass route 13 and the medicine 14 is dissolved. However, the press on the syringe downwardly from above is not always requisite.

The dissolution of the medicine 14 should be performed with visual observation or rate of flow into the front space 8 should be controlled to avoid the flow disturbance and all amounts of solvent is flown into the front space. The dissolution process finishes by tightening the fixer means 19, 19' on the middle and rear cases 4, 5. Thereafter the shoulder 24 of the plunger 7 is supported by the front end of the plunger retainer 20, and thereby the injection is kept at the complete status with overcoming possible back pressure occurred in the injection.

A needle holder 6 is mounted on the front of the syringe 1 before or after the injection is complete. A needle 25 is held to be penetrating the needle holder 6, and is mounted to penetrate the packing 10 so as to connect with the injection inside the ampule 2. In performing the injection, the needle is inserted into predetermined skin spot, and the injection will be injected by pushing on the rear end 21 of the plunger 7.

EXAMPLE 2

FIG. 3 shows a modified embodiment of the inventive injection syringe, wherein FIG. 3(a) shows the status before the dissolution of the unstable freeze dried medicine in longitudinally sectioned view, and FIG. 3(b) shows the status after the dissolution is complete also in longitudinally sectioned view.

This embodiment features in that the front case 3 and the middle case 4 shown in FIGS. 1 and 2 are made into one-piece, named the front case and numbered 17, in which the multichambered cylindrical ampule 2 is accommodated. The ampule 2 is fixed at its front end with the tapered tip portion 22 of the front case 17 and also fixed at its rear end with the inward flange or ampule stopper 48 provided at the rear end of the front case 17. The ampule stopper 48 is an inwardly extending flange, made from polypropylene, having a circular mouth at its center to admit the plunger 7 through and secured with the rear end of the front case 17.

The front case 17 and the rear case 35 are engaged with short threads or fixer means 19, 19' to produce more compact structure as compared with the basic embodiment in FIGS. 1 and 2. The operation required to prepare the injection from the stored medicine and the solvent is much the same as in the basic embodiment. That is, pushing on the plunger 7 forwardly causes the front and rear gaskets 11, 12 to advance and, upon the front gasket 11's entry into the bypass route 13's zone, the solvent or dispersing agent 15 stored in the rear space 9 starts flowing into the front space 8 through the bypass route 13 and an injection is prepared after the medicine 14 has been dissolved or dispersed.

Tightening the short threads or fixer means 19, 19' provided on the front and rear cases 17, 35, after all the solvent is flown into the front space 8, avoids the reverse move of the plunger 7 with aid of the retainer 20 and thereby the injection is kept at the complete status. In performing the injection whose operation is much the same as in the basic embodiment, that is, pushing on the plunger 7 allows the injection to inject through the needle holder 6.

EXAMPLE 3

FIG. 4 shows a further modified embodiment of the inventive injection syringe, wherein FIG. 4(a) shows the status before the dissolution of the solid medicine in longitudinally sectioned view, and FIG. 4(b) shows the status after the dissolution is complete also in longitudinally sectioned view.

This embodiment includes an additional device modified from the plunger 7 which is included in the basic embodiment as shown in FIGS. 1 and 2. A plunger 27, shown in FIGS. 4(a) and 4(b), has circumferential grooves 29 in stepwise arrangement at its midportion and a plunger retainer 28 has a nail or ratchet 30 at its inner most portion so as to mesh with the grooves 29. In performing the dissolution, pushing on the rear end 21 of the plunger 27 moves the plunger 27 and the plunger retainer 28 is unison, that is, the grooves 29 and the nail or ratchet 30 are moved in unison. In a process of dissolving the solid medicine 14, pushing on the rear case 5 toward the front of the ampule 2 causes the front gasket 11 and the rear gasket 12 through the plunger 27; and upon the front gasket 11's entry into the bypass route 13's zone, the solvent or dispersing agent 15 stored in the rear space starts flowing into the front space 8 through the bypass route 13 and an injection is prepared after the medicine 14 has been dissolved or dispersed.

Tightening the fixer means 19, 19' provided on the middle and rear cases 4, 5, after all the solvent is flown into the front space 8, avoids the reverse move of the plunger 7 with aid of meshing between the grooves 29 and the ratchet 30. Thereby the injection is kept at the complete status.

Referring to the combination of the plunger 27 and the retainer 28, more particularly the meshing between the grooves 29 and the ratchet 30. When the plunger 27 moves forwardly or upwardly in view of FIG. 4, the ratchet 30 allows the plunger 27 to move slipping or snapping through like step by step jump at respective grooves 29. But the plunger 27 is not allowed to move backwardly or downwardly in view of FIG. 4. Because of this function, the combination of the plunger 27 and the retainer 28 avoids the reverse move from back pressure occurred inside the ampule 2, a pair of nail are preferable as ratchets, however, any mechanism capable of allowing the one way move and stopping the reverse move may be technically applied to this device.

In performing the injection, pushing on the rear end 21 of the plunger 27 causes the grooved plunger 27 to advance by slipping through the ratchet 30 and thereby pushing on the rear end of the plunger 27, caused the front gasket 11 and rear gasket 12 in unison advance the injection is performed through the needle holder 6 in much the same way as noted above.

EXAMPLE 4

FIG. 5 shows a still further modified embodiment of the inventive injection syringe, wherein FIG. 5(a) shows the status before the dissolution of the unstable freeze dried medicine in longitudinally sectioned view, and FIG. 5(b) shows the status after the dissolution is complete also in longitudinally sectioned view.

This embodiment includes an additional device modified from the plunger 7 which is included in the basic embodiment as shown in FIGS. 1 and 2. A plunger 32, shown in FIGS. 5(a) and 5(b), is provided with thread portion covering length from its rear end to midpoint and a ring nut 34 having another thread 33' to determine an injection amount or dosage. Other structures or features included in this embodiment are much the same as the basic embodiment, as shown in FIGS. 1 and 2.

In performing the dissolution, pushing on the rear end 21 of the plunger 32 causes the front gasket 11 and the rear gasket 12 in unison to advance with aid of abutment at a shoulder 31 provided at midportion of the plunger 32; upon the front gasket 11's entry into the bypass route 13's zone, the solvent or dispersing agent 15 stored in the rear space 9 starts flowing into the front space 8 through the bypass route 13 and an injection is prepared after the medicine 14 has been dissolved or dispersed, and tightening the fixer means 19, 19' after the dissolution avoids the reverse move of the plunger 32, and the injection is kept at its complete status.

In determining the injection amount, this amount is determined by a length of the plunger's move. Accordingly, the nut 34 is turned to move and set an appropriate position and then, the plunger 32 is pushed to the stop point set by the nut 34 and thereby the injection with the predetermined amount is performed.

The injection will sometimes be performed more than one time using the same injection. However, mostly the injection finishes one time. For instance, certain predetermined amounts of the prepared injection will be injected and thereof excess amounts are normally cast away prior to the injection. In such a case, the device for determining an injection amount is useful to set an amount for casting away. The present invention includes such a preliminary operation.

EXAMPLE 5

FIG. 6 shows another still further modified embodiment of the inventive injection syringe, wherein FIG. 6(a) shows the status before the dissolution of the unstable freeze dried medicine in longitudinally sectioned view, and FIG. 6(b) shows the status after the dissolution is complete also in longitudinally sectioned view. The locking nut 39 included in this embodiment is shown of its details in FIG. 7. Specifically, FIG. 7(a) shows a schematic front view thereof; FIG. 7(b) shows a sectional view sectioned along the line A–A'; FIG. 7(c) shows a sectional view sectioned along the line B–B'.

This embodiment injection syringe includes a two-space cylindrical ampule 2, an outer case 37, a needle holder 6, and a plunger 36, wherein the ampule 2 is the same as in the basic embodiment as shown in FIGS. 1 and 2. The outer case 37 for accommodating the ampule 2 is unipartite or one-piece and has a front end 22 tapered to fix the front edge of the ampule 2 and also has an additional inner-space or lobe space 38 extending longitudinally to accommodate the bypass route 13 which projects outwardly like a lobe from the external surface of the ampule 2. The lobe space 38 avoids free rotation of the ampule 2 inside the case 37 and thereby there is eased the operation of engaging the front end of the plunger 37 with the rear gasket 12 in the ampule 2. Further, the clearance between the ampule 2 and the inner surface of the case 37 is allowed to be narrower. Thus, the stabler positioning of the ampule as well as the simpler configuration of the injection syringe is obtained.

The plunger 36 has the front end engaged with the rear gasket 12 and is mounted with the locking nut 39 which includes the locking structure to lock or fix the outer case 37 with the plunger 36 when the nut 39 stays at the rear end of the outer case 37 and to fix a position of the nut 39 itself when the nut 39 is apart from the rear end of the outer case 37, wherein unlocking function is also provided with the nut 39.

The structure of the locking nut 39 is shown in FIG. 7 divided into three subfigures. FIG. 7(a) shows a front view thereof. FIG. 7(b) shows a sectional view sectioned along A–A' line in FIG. 7(a). FIG. 7(c) shows a sectional view sectioned along B–B' line in FIG. 7(b). As shown, the locking nut 39 includes a base plate 40, brake shoe 42, 42', and a brake operator plate 41, wherein the outer case 37 and the plunger 36 are shown in dot lines at a viewing angle being taken from left to right in FIG. 6, that is, the case 37's and the plunger 36's center lines are assumed to be snugly viewed, and wherein, at the center portion of FIG. 7(b), two circles of an inner dot line one and an outer solid line one are drawn, and the former one is the plunger 36, and the latter one is the inside edge of the base plate 40.

The base plate 40 shaped to be generally a donut is mounted with pivot shafts 43, 43' to operate two brake shoes 42, 42' which are shaped to be generally a curved ellipsoid and provided each with a slot 44, 44'. The brake operator plate 41 and the brake shoes 43, 43' are connected with two stand shafts 45, 45' which further extend through two slots 44, 44' respectively to move or slide inside the slot 44, 44', and in turn, to turn the shoes 42, 42' about their pivot shafts 43, 43' respectively. Then, when the locking nut 39 is mounted on the plunger 36 at the rear end of the case 37, that is, at a position inside the case 37, the lobe 46 extending from the plate 40 acts as detente from free rotation of the nut 39.

Referring to the operation of the nut 39 with reference to FIG. 7(b) mainly, in braking or locking the nut 39, turning the operator plate 41 about 30 degrees clockwise causes the shafts 45, 45' to slide along the slots 44, 44', in turn, displaces the shoes to take positions (drawn in dot lines) 47, 47'. This displacement of shoes causes one end if the shoes (stand shaft side) is pressed to the internal surface of the outer case 37, in turn, the other end of the shoes is pressed to the external surface of the plunger 36, wherein each slot is shaped to be narrower as the shaft moves, and at the locking position, friction between the shaft 45, 45' and the slot 44, 44' stops the shaft 45, 45' at the locking position, then the outer case 37 is fixed to the plunger 36 through this displacement of the shoes 42, 42'.

In performing the unlocking, turning the operator plate 41 about 30 degrees counter clockwise causes the shoes 42, 42' to return to the initial positions (drawn in solid lines) 45, 45', and gaps between the internal surface of the outer case 37 and the break shoes are loosened, in turn, gaps between the external surface of the plunger 36 and the break shoes are loosened. This reversion loosens the locking action by the nut 39. That is, the nut 39 becomes free to move along the plunger 36. Where the nut 39 is at any position outside the case 37 or is apart from the rear end of the case 37, the nut's locking function effects to stop the nut itself at a position on the plunger 36. Then, the locking nut is not limited to what is described above in the present invention, rather there is acceptable such a structure including a spring and nob means wherein only while pressing the nob, it functions the spring to unlocking, such a structure including means for fixing the outer case with the plunger or fixing the nut with the plunger, incorporated with reversible means.

In performing the dissolution, unlocking the nut 39 and pushing on the rear end 21 of the plunger 36, upon the front gasket 11's entry into the bypass route 13's zone, the solvent or dispersing agent 15 stored in the rear space 9 starts flowing into the front space 8 through the bypass route 13 and an injection is prepared after the medicine 14 has been dissolved or dispersed. After all the solvent is flown into the front space 8, locking the nut 39 at the rear end of the case 37 avoids the reverse move of the gasket 12 to keep the injection at the complete status.

In performing the injection, the nut 39 is set on the plunger 36 at the position for a predetermined dosage amount, and pushing on the rear end 21 of the plunger 36 performs the injection, that is, the plunger 36 stops when the nut 39 reaches the rear end of the case 37. The same operation is applicable to the preliminary casting away of the injection.

It is possible to mount a needle holder 6 on the front of the syringe before preparing the injection depend on the character of medicine 14, in the present application.

Normally the needle holder 6 is mounted with the needle 25 which penetrates through the holder. However, the present invention includes a modification wherein the needle is converted, by special attachment, to a circular cone shaped nozzle for the purpose of obtaining fitness to a tridirectional valve leading to a catheter. In this modification, such a nozzle has a larger diameter than the normal needle for the injection.

What is claimed is:

1. An injection syringe comprising a multichambered cylindrical ampule; a tripartite case having a front case, a middle case, a rear case, and a needle holder; and a plunger, wherein:

the multichambered cylindrical ampule includes at least two chambers of a front space and a rear space, the front space being sealed forwardly with a packing penetrable by a needle an sealed rearwardly with a movable front gasket, and the rear space being sealed forwardly with the front gasket and sealed rearwardly with a movable rear gasket, and the ampule further including a bypass route longitudinally arranged on an inner surface of the ampule such that the front gasket is located to take a position rearwardly from the bypass route before dissolution of a solid medicine, such that the front space, which is configured to receive a solid medicine, is separated from the rear space, which is configured to receive a medicinal solvent or dispersing agent, thereby the solid medicine and the solvent or dispersing agent being separately stored;

the front case includes a tapered tip portion configured to fix a front edge of the ampule inside thereof, and a first fixer device provided externally at a rear end thereof; the middle case including a second fixer device provided internally at a front end thereof, and a flange provided internally at the rear end thereof to fixedly accommodate the ampule inside a housing formed of the front case and the middle case by tightening the first and second fixer devices;

the middle case further includes a third fixer device provided externally at midportion thereof, and the rear case including a fourth fixer device provided internally at a front end thereof and also a plunger retainer provided internally at a rear end thereof the plunger being mounted in place by the plunger retainer and engaged at a front end of the plunger with a rear gasket;

whereby, in a process of dissolving the solid medicine, pushing on the rear case toward the front of the ampule causes the front gasket and the rear gasket in unison to advance with aid of abutment at a shoulder provided at midportion of the plunger; upon the front gasket's entry into a bypass route zone, the solvent or dispersing agent stored in the rear space starts flowing into the front space through the bypass route and an injection is prepared after the medicine has been dissolved or dispersed; then, tightening the third and fourth fixer devices to connect the middle case with the rear case avoids a reverse move of the shoulder with aid of the retainer to keep the injection at a complete status, and pushing on the rear end of the plunger performs the injection through the needle holder; thereby completing the injection with use of an unstable injection.

2. An injection syringe for an unstable freeze dried medicine, including a device for preparation of an injection comprising a multichambered cylindrical ampule; a tripartite case having a front case, a middle case, a rear case, and a needle holder; and a plunger, wherein:

the multichambered cylindrical ampule includes at least two chambers of a front space and a rear space, the front space being sealed forwardly with a packing penetrable by a needle and sealed rearwardly with a movable front gasket, and the rear space being sealed forwardly with the front gasket and sealed rearwardly with a movable rear gasket, and the ampule further including a bypass route longitudinally arranged on an inner surface of the ampule such that the front gasket is located rearwardly of the bypass route before dissolution of an unstable freeze dried medicine wherein the front space for containing said medicine is separated from the rear space for containing a medicinal solvent or dispersing agent;

the front case includes a tapered tip portion configured to fix a front edge of the ampule inside thereof, and a first fixer device provided externally at a rear end thereof, the middle case including longitudinally on an inner surface thereof a recess for receiving the bypass route and including a second fixer device provided internally at a front end thereof, and a flange provided internally at the rear end thereof to fixedly accommodate the ampule inside a housing formed of the front case and the middle case by tightening the first and second fixer devices;

the middle case further includes a third fixer device provided externally at midportion thereof, and the rear case including a fourth fixer device provided internally at a front end thereof, and also a plunger retainer provided internally at a rear end thereof, the plunger being mounted in place by the plunger retainer and engaged at a front end of the plunger with a rear gasket;

whereby, in a process of dissolving the unstable freeze dried medicine, pushing on the rear case toward the front of the ampule causes the front gasket and the rear gasket in unison to advance with aid of abutment at a shoulder provided at midportion of the plunger; then the front gasket enters into a bypass route's zone, the solvent or dispersing agent is released to flow into the front space through the bypass route such that an injection is prepared after the medicine has been dissolved or dispersed; then, tightening the third and fourth fixer devices to connect the middle case with the rear case avoids a reverse move of the shoulder with aid of the retainer, thus the prepared injection is maintained at a complete status, and pushing on the rear end of the plunger performs the injection through the needle holder; thus environmentally sensitive nature of the injection is overcome.

3. In a process for preparation of an injection applicable to unstable freeze dried medicine, with use of an injection syringe, said syringe, including a multichambered cylindrical ampule, a front case, a middle case, a rear case, a needle holder, and a plunger, said multichambered cylindrical ampule including two chambers of a front space and a rear space, the front space being sealed forwardly with a packing penetrable by a needle and sealed rearwardly with a movable rear gasket, and the ampule also including a bypass route longitudinally arranged on inner surface of the ampule such that the front gasket is located to take a position rearwardly apart from the bypass route before dissolution of an unstable freeze dried medicine, and wherein the ampule is set fixedly inside the front case and the middle case, and rear gasket is connected with the plunger;

said process comprising the step of; containing the unstable freeze dried medicine into the front space and filling the rear space with a medical solvent or dispersing agent; erecting the injection syringe thus prepared in a front-up and rear-down status, pressing manually the injection syringe downwardly by the force acting on the plunger and at the moment that the front gasket enters into the bypass route zone, the solvent or dispersing agent filled in the rear space flows into the bypass route to dissolve or disperse the unstable freeze dried medicine in the front space wherein a flow rate is monitored and controlled manually by observation of a dissolving condition of said medicine, maintained in a laminar flow sate so as into the cause stirring and shaking during the dissolution; tighten by meshing thread parts or fixer means connecting the middle and rear cases after all solvent has been sent off the rear space, to avoid a reverse move of the gasket, thus the prepared injection is maintained ready to use.

* * * * *